(12) United States Patent
Keller

(10) Patent No.: US 8,313,232 B2
(45) Date of Patent: Nov. 20, 2012

(54) DYNAMIC MIXER

(75) Inventor: Wilhelm A. Keller, Merlischachen (CH)

(73) Assignee: Sulzer Mixpac AG, Rotkreuz (CH)

( * ) Notice: Subject to any disclaimer, the term of this patent is extended or adjusted under 35 U.S.C. 154(b) by 750 days.

(21) Appl. No.: 12/083,145

(22) PCT Filed: Oct. 3, 2006

(86) PCT No.: PCT/CH2006/000538
§ 371 (c)(1),
(2), (4) Date: Jul. 1, 2009

(87) PCT Pub. No.: WO2007/041878
PCT Pub. Date: Apr. 19, 2007

(65) Prior Publication Data
US 2009/0296516 A1 Dec. 3, 2009

(30) Foreign Application Priority Data
Oct. 7, 2005 (CH) .................................... 1619/05

(51) Int. Cl.
*B01F 7/20* (2006.01)
(52) U.S. Cl. .................................. 366/162.3; 366/177.1
(58) Field of Classification Search ................ 366/155.1, 366/162.3, 172.1, 177.1, 181.6
See application file for complete search history.

(56) References Cited

U.S. PATENT DOCUMENTS

| 6,394,643 B1 * | 5/2002 | Bublewitz et al. ......... 366/172.1 |
| 6,443,612 B1 * | 9/2002 | Keller ............................ 366/307 |
| 2001/0005338 A1 * | 6/2001 | Muhlbauer et al. ........... 366/307 |

FOREIGN PATENT DOCUMENTS

| DE | 42 35 736 C1 | 3/1994 |
| DE | 299 07 573 U1 | 9/2000 |
| DE | 100 43 489 A1 | 3/2002 |
| DE | 10 2004 008 748 A1 | 9/2004 |
| EP | 1 106 243 A2 | 6/2001 |
| EP | 1 510 249 A1 | 3/2005 |
| WO | WO 2004/080611 A1 | 9/2004 |

* cited by examiner

*Primary Examiner* — David Sorkin
(74) *Attorney, Agent, or Firm* — Kilpatrick Townsend & Stockton LLP

(57) ABSTRACT

A dynamic mixer for mixing components in different volumetric amounts comprises a rotor housing which is closed on the inlet side thereof by a cover, the cover defining inlets for the components. The inlet for the first component having the larger volumetric amount leads to an antechamber that communicates with a following mixing chamber by at least one passage. The mixing rotor includes a distributor body located in the antechamber for distributing the first component around the axis of rotation of the mixing rotor. The inlet for the second component having the smaller volumetric amount leads to at least one inlet opening located in the area of the passage to the mixing chamber transversely to the axis of rotation.

12 Claims, 6 Drawing Sheets

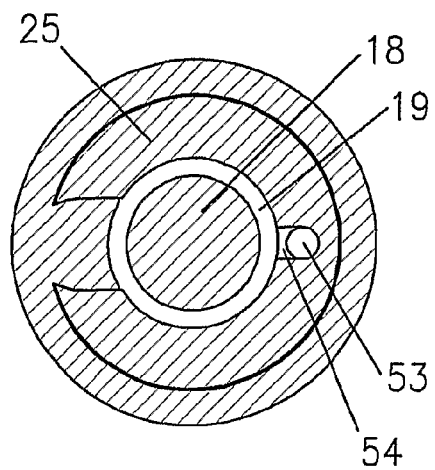
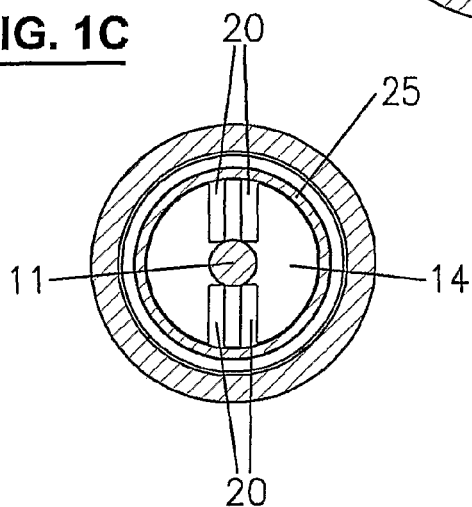
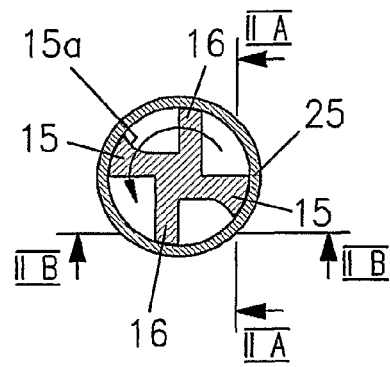
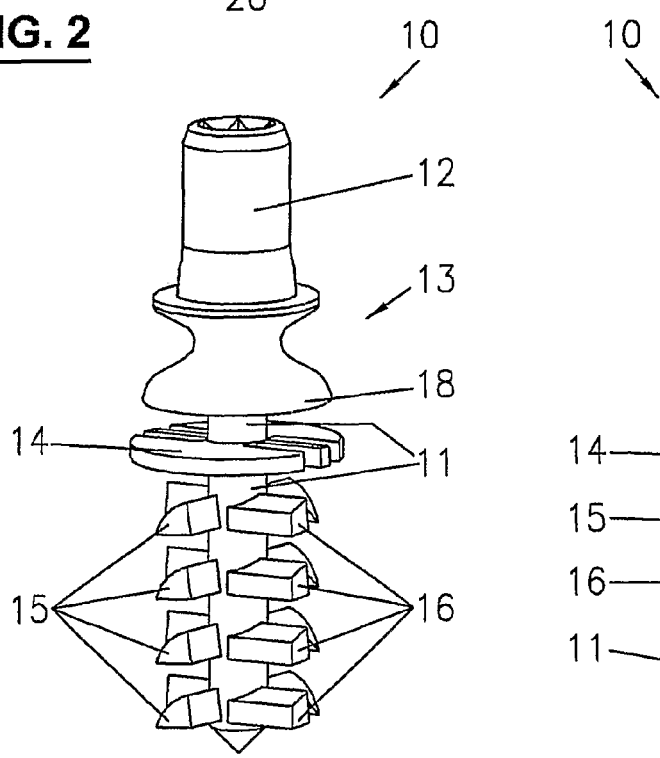
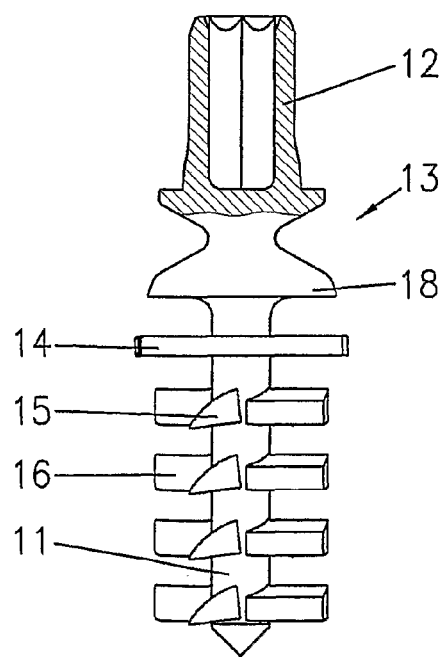

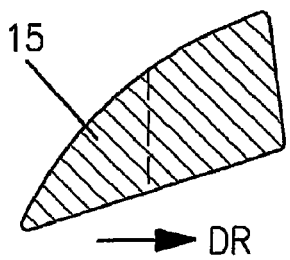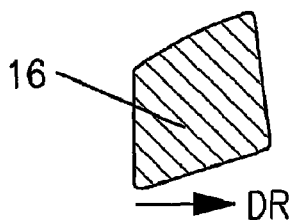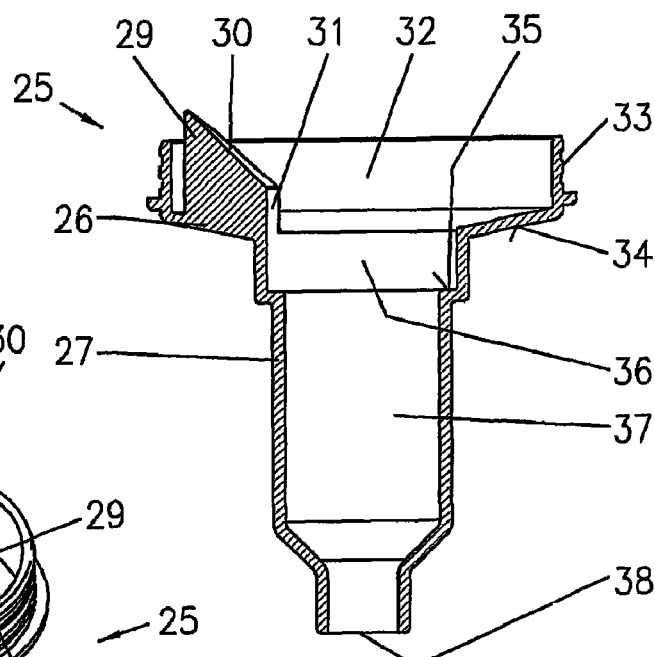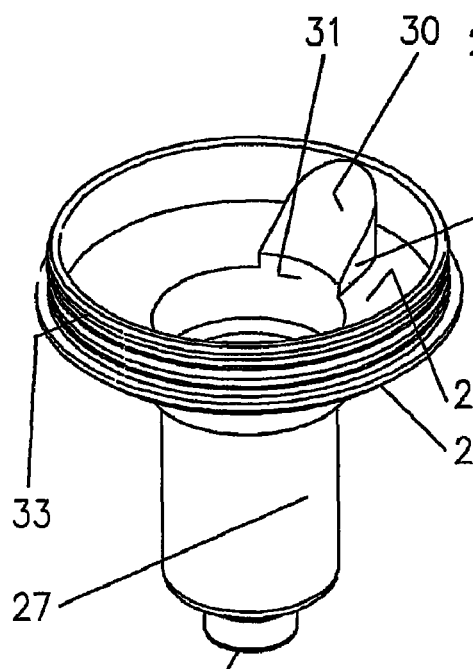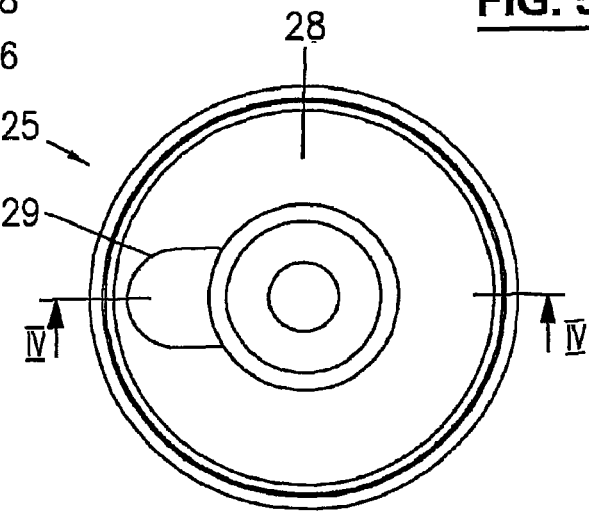

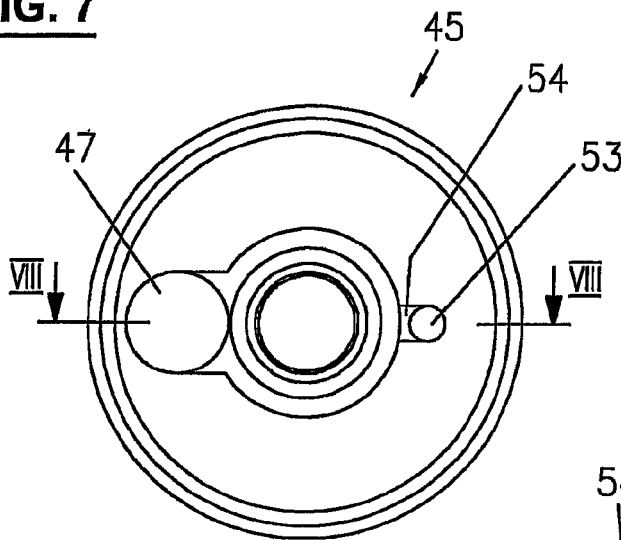
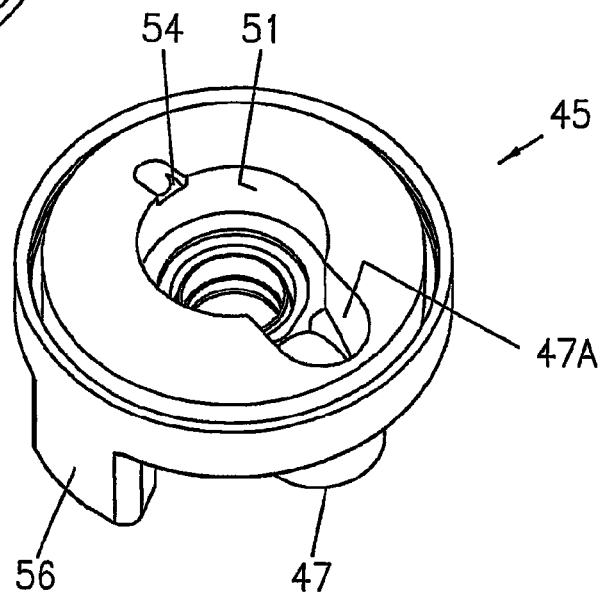
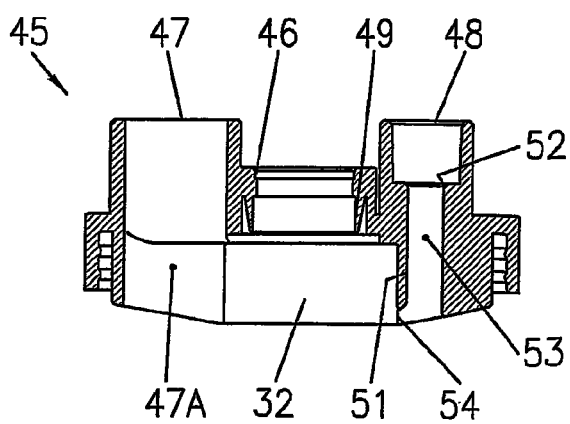

DYNAMIC MIXER

CROSS-REFERENCES TO RELATED APPLICATIONS

This application is a National Stage of International Application No. PCT/CH2006/000538, filed Oct. 3, 2006, and which claims the benefit of Swiss Patent Application No. 1619/05, filed Oct. 7, 2005, the disclosures of both applications being incorporated herein by reference.

BACKGROUND OF THE INVENTION

The present invention relates to a dynamic mixer, comprising a rotor housing in which a mixing rotor is arranged and which is closed on the inlet side by a cover on which inlets for the components are arranged.

Particularly when mixing components in different volumetric amounts as they are e.g. used for producing dental impression materials the difficulty arises that the two components should be mixed at the correct mixing ratio at the beginning of the mixing process already. If no particular measures are taken, the component whose volumetric content is smaller, e.g. a catalyst, is absent or not present in a sufficient amount at the beginning of the paste strand discharged from the mixer. The result is an unsatisfactory mixing quality such that e.g. the hardening capability of the casting compound is not ensured. Another weakness of the currently available mixers is the inclusion of air bubbles, which affects the impression quality.

EP-A2-1 402 940 discloses a dynamic mixer having a detour channel in order to retard the entrance of the component having the larger volumetric amount into the mixing chamber. This measure has the disadvantage that a high pressure is required for delivering that component to the mixing chamber through the detour channel, particularly if it is highly viscous.

BRIEF SUMMARY OF THE INVENTION

On the background of this prior art, the object of the present invention is to provide a dynamic mixer ensuring, in a simple manner and without additional pressure losses, that both components are mixed at the correct ratio without suppressing one of the components, and that air inclusions are avoided.

A dynamic mixer attaining this object is defined in claim 1. The further claims, more particularly claim 2, define preferred embodiments.

The invention will be explained in more detail hereinafter with reference to drawings of exemplary embodiments.

BRIEF DESCRIPTION OF THE DRAWINGS

FIG. 1B shows a section according to line IB-IB in FIG. 1, without the bayonet ring, FIG. 1C shows a section according to line IC-IC in FIG. 1, without the bayonet ring, FIG. 1D shows a section according to line ID-ID in FIG. 1, without the bayonet ring, FIG. 2 shows a perspective view of the mixing rotor of FIG. 1, FIG. 2A shows a section of mixing blade 15 according to line IA-IA in FIG. 1D, FIG. 2B shows a section of mixing blade 16 according to line IB-IB in FIG. 1D, FIG. 3 shows a lateral view and partial section of the mixing rotor of FIG. 2;

FIG. 4 shows a section according to line IV-IV in FIG. 5 of the rotor housing of FIG. 1, FIG. 5 shows the rotor housing of FIG. 4 as seen from the inlet side, FIG. 6 shows a perspective view of the rotor housing of FIG. 4, FIG. 7 shows the cover of the rotor housing of FIG. 6 as seen from the outlet side, FIG. 8 shows a section according to line VIII-VIII in FIG. 7, FIG. 9 shows a perspective view of the rotor housing cover of FIG. 7.

DETAILED DESCRIPTION OF THE INVENTION

Figure 1:
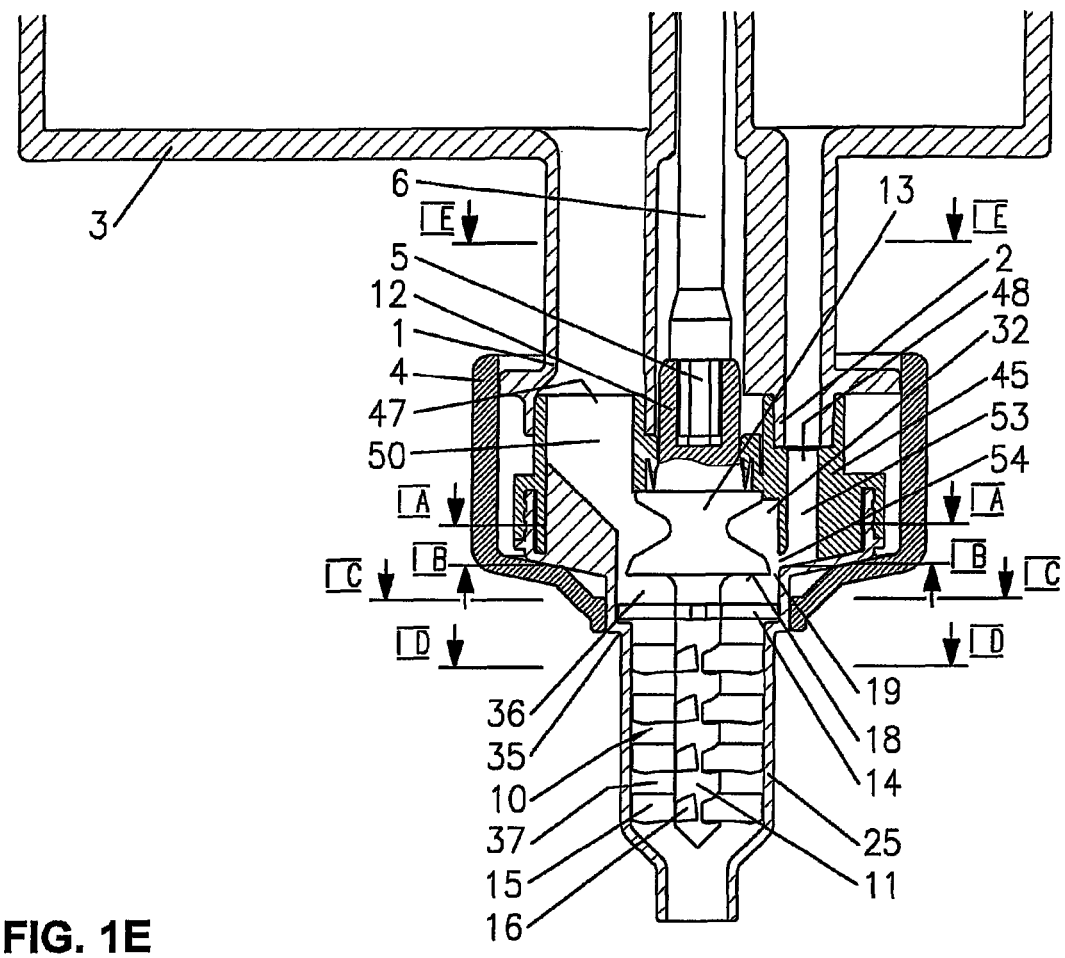
FIG. 1 shows a side elevation and partial section of a first exemplary embodiment of a mixer according to the invention that is secured to a cartridge by means of a bayonet ring.
Figure 1E:
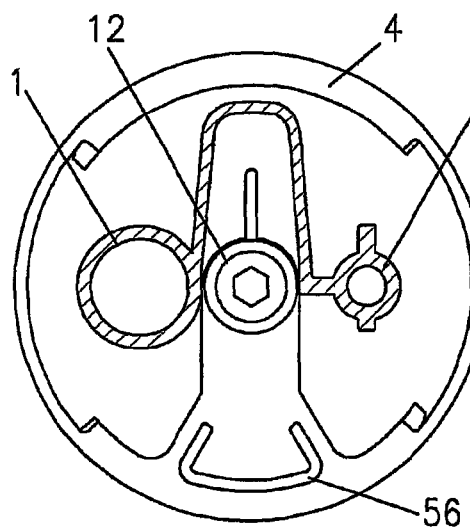
FIG. 1E shows a section according to line IE-IE in FIG. 1, without the bayonet ring.
Figure 1A:
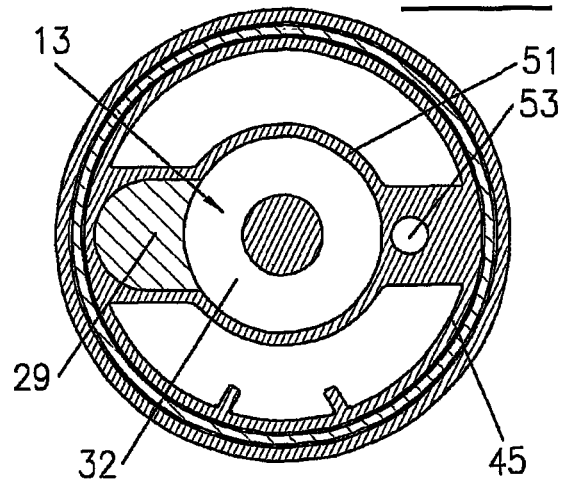
FIG. 1A shows a section according to line IA-IA in FIG. 1, without the bayonet ring.

FIG. 1 shows the dynamic mixer which is connected to larger outlet 1 and smaller outlet 2 of a double cartridge 3 and secured by means of a bayonet ring 4 and which serves for mixing two components in different volumetric amounts. Hereinafter, the component having the larger volumetric amount will be designated as component A and the component having the smaller volumetric amount as component B.

The mixer includes a mixing rotor 10, a rotor housing 20 and rotor housing cover 30. In order to set mixing rotor 10 in rotation, it is coupled on the inlet side to a driver 5 of mixer drive shaft 6.

As appears in FIGS. 2 and 3, the inlet end of mixing rotor 10 comprises a driver hub 12 having an opening for engagement with driver 5.

Driver hub 12 has a distributor body 13 located on its inlet side as well as a disk portion 14 and mixing blades 15 and 16, respectively, arranged on following rotor hub 11.

Distributor body 13 has a longitudinal cross section that is curved toward rotor hub 11. End portion 18 of distributor body 13 facing disk portion 14 has a circular rim, also shown in FIG. 1B. In the assembled condition of the mixer, this rim is located at a distance from the wall of rotor housing 25 such that a gap forming a passage 19 results between the rim of end portion 18 and the wall of rotor housing 25.

As appears in FIG. 1C, disk portion 14 has passageways 20 in the form of slots extending from rotor hub 11 to the edge of disk portion 14. Different passageways and shapes of the latter may alternatively be provided.

Mixing blades 15, 16 are arranged on rotor hub 11 in multiple planes. The shape of mixing blades 15, 16 is designed for favorable flow characteristics, i.e. it is chosen such that the components do not detach therefrom during the mixing operation, thereby avoiding the inclusion of unwanted air bubbles. On each level of rotor hub 11, mixing blades 15 having an essentially rhomboid cross-section, see FIG. 2A and mixing blades 16 having an essentially rhomboid cross-section as well (see FIG. 2B) are alternatingly arranged. In FIG. 1, the direction of rotation of the mixing rotor is indicated by an arrow, and in FIGS. 2A and 2B, the direction of rotation is indicated by DR.

In FIG. 1 and in cross-section 1D transversally to the axis of rotation of mixing rotor 10, mixing blade 16 has a rectangular shape while mixing blade 15 is curved in the shape of a hook on its side 15a turned away from the rotational direction. In an advantageous embodiment, the end portions of all mixing blades are curved and hook-shaped on their sides turned away from the rotational direction.

Mixing rotor 10 is enclosed in a rotor housing 25 closed by a rotor housing cover 45 that is illustrated in FIGS. 4 to 6. Rotor housing 25 comprises a disk-shaped housing portion 26 receiving rotor housing cover 45 as well as a cylindrical housing portion 27 receiving rotor hub 11 with mixing blades 15 and 16. On bottom surface 28 of disk-shaped housing portion 26, a deflecting body 29 is arranged whose upper side 30 is slanted and forms part of an inlet channel 50 for component A and whose front side 31 forms part of an antechamber 32, cf. FIG. 1.

Disk-shaped housing portion 26 further comprises grooves 33 for forming a snap connection with rotor housing cover 45 and a bearing surface 34 for bayonet ring 4. Cylindrical housing portion 27 has a step 35 on which disk portion 14 of mixing rotor 10 is rotatably seated whereby cylindrical housing portion 27 is divided into a mixing chamber 36 and a post-mixing chamber 37. The end of cylindrical housing portion 27 forms mixer outlet 38.

FIGS. 7 to 9 show rotor housing cover 45 including a rotor bearing 46 for receiving driver hub 12 as well as two inlets 47 and 48 for component A and B, respectively. For a tight seal of driver hub 12, rotor housing cover 45 comprises a sealing lip 49.

Inlet 47 for component A has a larger cross-section than inlet 48 for component B and leads via a channel 50 to antechamber 32 that is partly confined by a wall 51 constituted by a recess 47A formed in the bottom plate of rotor housing cover 45. Smaller inlet 48 leads to the area of passage 19 at the end of antechamber 32 via a step 52 and an essentially cylindrical inlet channel 53 and inlet aperture 54. "In the area of the passage" means that the inlet may be located either in front of or after or opposite the passage, depending on the volumetric ratio of the components and the design of the distributor body.

The rim of rotor housing cover 45 is provided with grooves 33 for forming a snap connection with grooves 33 of rotor housing 25. Rotor housing cover 45 further comprises mechanical coding means, f. ex. in the form of a coding nose 56 directed toward inlets 47 and 48 fitting into a corresponding recess in cartridge 3, thereby allowing the attachment of the mixer to cartridge 3 in a defined orientation only, see sectional view 1E.

In the attached condition of the mixer according to FIG. 1, the larger outlet 1 of cartridge 3 is pushed over the larger inlet 47 of the mixer while outlet 2 is pushed into smaller inlet 48 up to step 52, see FIG. 8.

Deflecting body 29 shown in FIG. 6 is located at the end of inlet channel 50 such that its upper side 30 forms part of inlet channel 50, which leads into antechamber 32 essentially radially with respect to the axis of rotation. Distributor body 13 is arranged in antechamber 32, the latter being confined by the front side 31 of deflecting body 29 and by circular wall 51 of cover 45 shown in FIG. 7. Inlet aperture 54 of inlet channel 53 leads into antechamber 32 essentially radially.

In the mixing operation within the mixer according to FIG. 1, component A is pressed through inlet channel 50 into antechamber 32, guided around the axis of rotation and distributed over the entire cross-section by rotating distributor body 13, and delivered through the passage, i.e. annular gap 19, to mixing chamber 36 in the form of a thin, continuous layer on the entire circumference. Component B is radially delivered through inlet aperture 54 onto the rotating end portion 18 of distributor body 13 and regularly distributed, as a result of the existing flow and shearing conditions, on the circumference of end portion 18 and premixed with component A.

Due to the presence of an antechamber 32, the transport of component A is temporally retarded with respect to component B so that component A reaches mixing chamber 36 a little later than component B rather than before the latter. In this manner it is ensured that the first portion of the mixture also corresponds to the desired mixing ratio. Driven distributor body 13 allows an air-free filling of antechamber 32 with component A as well as its dynamic distribution which, in contrast to a mixer having a stationary detour channel, offers the advantage that the flow resistance remains small. Furthermore, the geometry of inlet channel 50, leading from inlet 47 to antechamber 32 by the shortest possible way, also avoids an increase of the flow resistance so that the required delivery pressure in cartridge 3 and the stresses acting on the dispensing device are altogether low.

When the two premixed components have reached mixing chamber 36, they are essentially directed radially from the periphery toward the center while a further mixing effect results due to the existing flow and shearing conditions. After its passage through slotted disk portion 14, the mixture fills up post-mixing chamber 37 on the entire cross-section thereof and is subjected to another shearing and shifting process. The selected shape of mixing blades 15 and 16 avoids an inclusion of air and thereby prevents the formation of bubbles in the mixture. After flowing through the post-mixing chamber, the mixed composition is finally discharged through mixer outlet 38.

Figure 10:
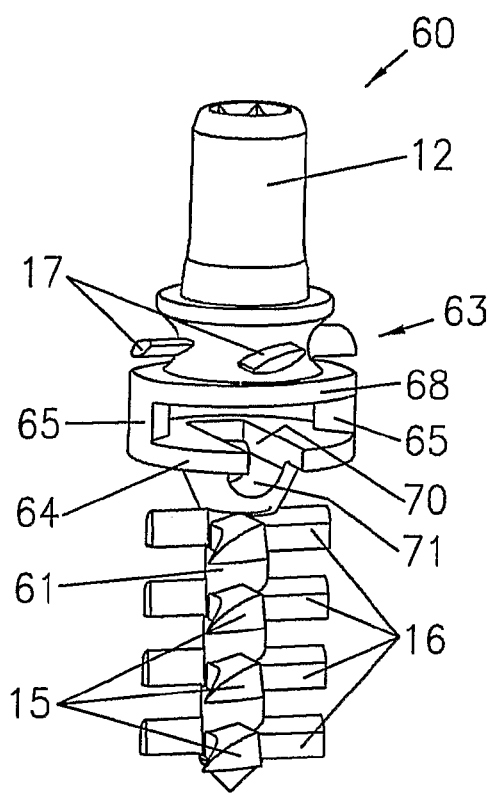
FIG. 10 shows a perspective view of a second exemplary embodiment of a mixing rotor.
Figure 11:
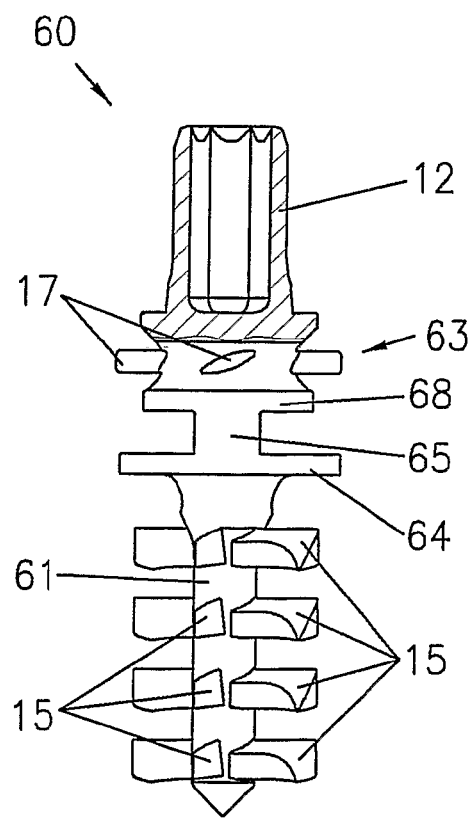
FIG. 11 shows a lateral view and partial section of the mixing rotor of FIG. 10.
Figure 12:
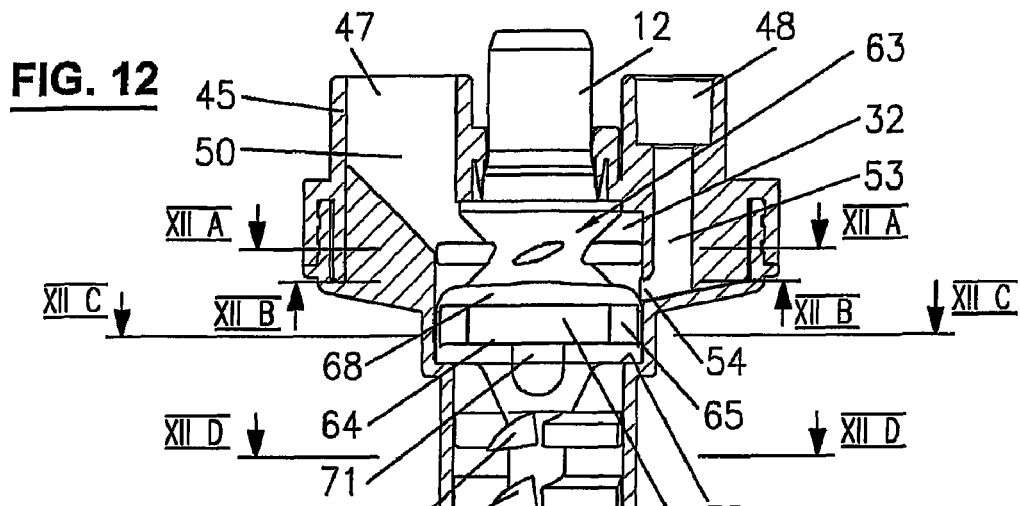
FIG. 12 shows a lateral view and partial section of an assembled mixer including the mixing rotor of FIG. 11.

FIGS. 10 and 11 show another embodiment of mixing rotor 60 which is a part of the mixer illustrated in FIG. 12. Components that are equivalent to the mixer according to FIG. 1 are designated by the same reference numerals. The required feed pressure is further reduced by conveyor blades 17 provided on distributor body 63 in antechamber 32.

Figure 12A:
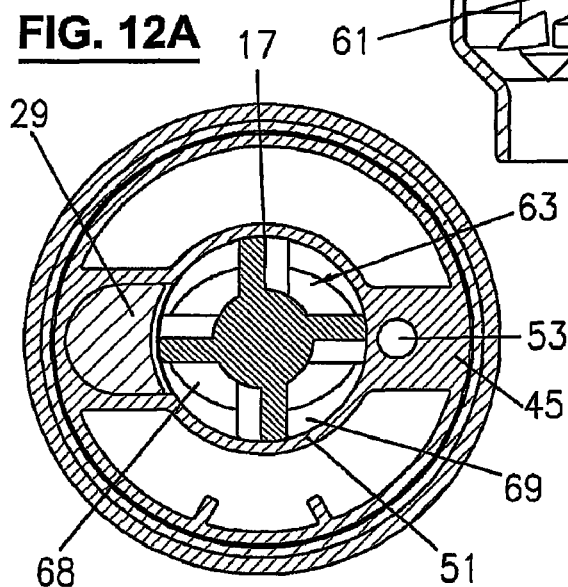
FIG. 12A shows a section according to line XIIA-XIIA in FIG. 12.

As appears in the sectional view of FIG. 12A, end portion 68 of distributor body 63 has an oval shape such that a passage 69 in the form of two rotating gaps results between end portion 68 and the wall of rotor housing 25.

Figure 12B:
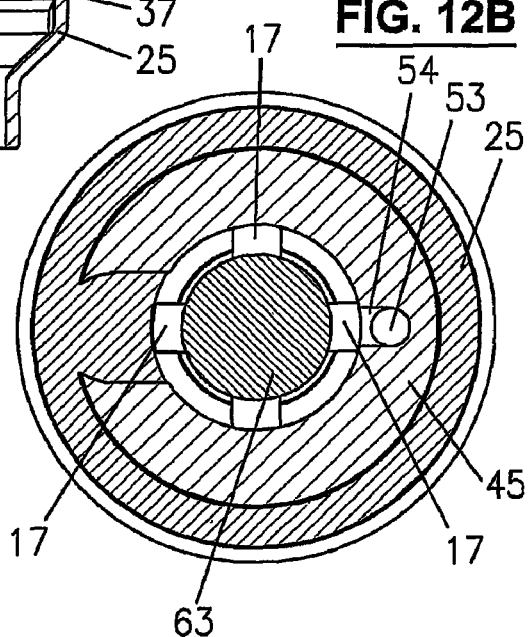
FIG. 12B shows a section according to line XIIB-XIIB in FIG. 12.

FIG. 12B shows the end of channel 53, leading to the edge of end portion 68 of distributor body 63 in antechamber 32 through inlet opening 54.

Figure 12C:
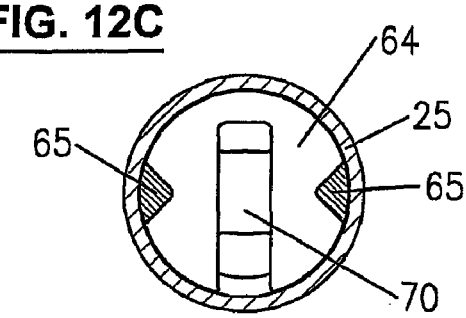
FIG. 12C shows a section according to line XIIC-XIIC in FIG. 12.

End portion 68 of distributor body 63 is connected by two lateral ridges 65 to a disk portion 64 having a passage aperture 70 in the form of a slot. cf. FIGS. 10 and 12C. Passage aperture 70 extends from the edge of disk portion 64 through its center up to the area near the opposite edge thereof, cf. FIG. 12C.

As further appears in FIG. 11, at the edge of its passage aperture, disk portion 64 is connected to rotor hub 61 in such a way that a preponderantly central passage 71 from mixing chamber 36 to post-mixing chamber 37 results.

Figure 12D:
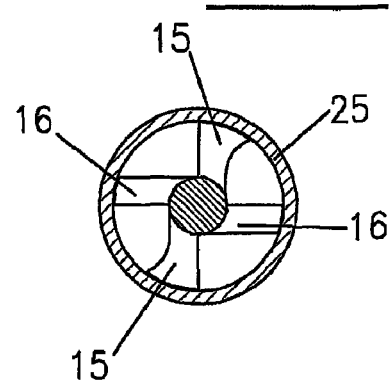
FIG. 12D shows a section according to line XIID-XIID in FIG. 12.

Mixing blades 15 and 16, arranged in multiple planes on rotor hub 61, are designed for favorable flow characteristics in order to avoid the inclusion of air bubbles cf. FIGS. 1D and 12D.

In the mixing operation within the mixer according to FIG. 12, component A is pressed through inlet channel 50 into antechamber 32, guided around the axis of rotation and distributed over the entire cross-section by rotating distributor body 63, and delivered through the rotating passages 69 to mixing chamber 36 in the form of a thin, continuous layer. Component B is introduced into antechamber 32 radially and premixed with component A. On the outlet side of mixing chamber 36, the components are further mixed in combination with passage aperture 70 and central passage 71 and subsequently reach post-mixing chamber 37 where they are post-mixed and finally discharged.

In the mixer according to FIGS. 1 and 12, inlet opening 54 to antechamber 32 is arranged in the area of passage 19 or 69, respectively. It is conceivable to provide more than one inlet opening 54 in order to be able to introduce component B in multiple locations. It is further conceivable to arrange inlet opening 54 after passage 19 or 69, respectively, for example in such a manner that inlet channel 53 ends in mixing chamber 36.

The optimized design of the mixing operation and the central arrangement of the different mixing elements allow a smaller pressure loss and a reduced mixer drive torque. The reduced friction in the medium reduces energy consumption, thereby resulting in a reduced temperature increase of the mixed material.

The represented arrangements according to FIGS. 1 and 12 have been described for the case that the volumes of two components are different from each other and that the component having the smaller volumetric amount is therefore delivered to the antechamber in the area of the passage in order to achieve a maximum premixing action. However, the design of the dynamic mixer offers the same advantages when both components have the same volume. In this case, the two components are symmetrically delivered to the antechamber in the upper area thereof in order to be distributed and premixed therein by the distributor body and to reach the mixing chamber through the passage.

In the embodiment having equal volumetric amounts, the inlets and outlets, respectively, are generally identical and the inlets are insertable into the outlets; but other variants are also possible where the outlets are insertable into the inlets.

Furthermore, more than only one additional, smaller component may be admixed to the larger component. In this case, another inlet as well as another channel having an inlet opening near the passage are required. The depicted and disclosed characteristic features may be combined with each other as desired.

The invention claimed is:

1. A dynamic mixer for mixing two or more components, comprising:
    a rotor housing which is closed on an inlet side thereof by a cover, wherein the cover defines inlets for the components;
    an antechamber defined in the rotor housing, in fluid communication with the inlets;
    a mixing chamber defined in the rotor housing, in fluid communication with the antechamber via at least one passage; and
    a mixing rotor disposed in the rotor housing and comprising a distributor body disposed in the antechamber and mixing blades disposed in the mixing chamber;
    wherein a downstream end of the distributor body is flared in a downstream direction for distributing the components outward, away from an axis of rotation of the mixing rotor.

2. The dynamic mixer according to claim 1, the mixer being configured for mixing the components in different volumetric amounts from one another, wherein the components comprise a first component having a larger volumetric amount and a second component having a smaller volumetric amount,
    wherein the inlets comprise:
        a first inlet for the first component, wherein the first inlet ends in an upstream area of the antechamber, and
        a second inlet for the second component;
    the mixer further comprising at least one inlet opening defined in the rotor housing, disposed near the passage, wherein the second inlet ends in the inlet opening.

3. The dynamic mixer according to claim 1, the mixer being configured for mixing the components in equal volumetric amounts, wherein each of the inlets ends in an upper area of the antechamber.

4. The dynamic mixer according to claim 1, where the passage comprises at least one gap between an edge of the distributor body and a wall of the rotor housing or of the rotor housing cover.

5. The dynamic mixer according to claim 2, wherein the inlet opening is configured such that the second component is delivered therethrough essentially transversally to the axis of rotation of the mixing rotor.

6. The dynamic mixer according to claim 1, wherein the mixing rotor further comprises a disk having at least one passage aperture, wherein the disk is disposed downstream of the antechamber.

7. The dynamic mixer according to claim 6, wherein the mixing chamber is essentially defined between a wall of the rotor housing, an outlet side of the distributor body, and an outlet side of the disk, and wherein the passage aperture is configured such that the components, while flowing through the mixing chamber, are essentially deflected toward the axis of rotation.

8. The dynamic mixer according to claim 6, wherein the rotor housing defines a constricting step that serves as a support for the disk and blocks fluid communication between the mixing chamber and an additional, downstream post-mixing chamber at a periphery of the mixing chamber.

9. The dynamic mixer according to claim 1, wherein the distributor body comprises conveyor blades disposed thereon.

10. The dynamic mixer according to claim 9, wherein each of the mixing blades comprises an essentially rhomboid cross-section, wherein at least some of the mixing blades comprise a drop- or hook-shaped end on a side disposed away from a direction of rotation.

11. The dynamic mixer according to claim 1 in combination with a cartridge configured to dispense the components,
    the mixer and the cartridge being configured for dispensing and mixing the components in different volumetric amounts from one another,
    wherein the inlets comprise a larger inlet and a smaller inlet;
    wherein the cartridge comprises a larger outlet and a smaller outlet,
    wherein the larger outlet is slidable over the larger inlet and the smaller outlet is insertable in the smaller inlet.

12. The dynamic mixer according to claim 1 in combination with a cartridge configured to dispense the components,
    wherein the rotor housing cover of the mixer and the cartridge comprise corresponding coding elements in order to allow attachment of the mixer to the cartridge in only one particular orientation.

* * * * *